US006799572B2

(12) United States Patent
Nichols et al.

(10) Patent No.: US 6,799,572 B2
(45) Date of Patent: Oct. 5, 2004

(54) DISPOSABLE AEROSOL GENERATOR SYSTEM AND METHODS FOR ADMINISTERING THE AEROSOL

(75) Inventors: Walter A. Nichols, Chesterfield, VA (US); F. Murphy Sprinkel, Jr., Glen Allen, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 35 days.

(21) Appl. No.: 09/742,321

(22) Filed: Dec. 22, 2000

(65) Prior Publication Data

US 2002/0078955 A1 Jun. 27, 2002

(51) Int. Cl.[7] ................................................ A61M 16/00

(52) U.S. Cl. ............................ 128/203.26; 128/203.12; 128/203.17; 128/203.21; 128/203.27

(58) Field of Search ....................... 128/203.12, 203.17, 128/203.25, 203.27, 203.28, 203.15, 203.21

(56) References Cited

U.S. PATENT DOCUMENTS

| | | | |
|---|---|---|---|
| 2,896,856 | A | 7/1959 | Kravits |
| 3,084,698 | A | 4/1963 | Smith |
| 3,157,179 | A | 11/1964 | Paullus et al. |
| 3,162,324 | A | 12/1964 | Houser |
| 3,431,393 | A | 3/1969 | Katsuda |
| 3,486,663 | A | 12/1969 | Humphrey |
| 3,716,416 | A | 2/1973 | Adlhart et al. |
| 3,750,961 | A | 8/1973 | Franz |

(List continued on next page.)

FOREIGN PATENT DOCUMENTS

| | | | |
|---|---|---|---|
| EP | 0358114 | A | 3/1990 |
| EP | 0642802 | A2 | 5/1996 |
| HU | 168128 | B | 11/1977 |
| HU | 216121 | B | 3/1991 |
| HU | P953409 | | 6/1994 |
| WO | 94/09842 | A | 5/1994 |
| WO | 98/17131 | | 4/1998 |

OTHER PUBLICATIONS

Notification of Transmittal of the International Search Report or the Declaration dated Mar. 6, 2003 for PCT/US02/38910.

Written Opinion dated Nov. 4, 2003 for PCT/US01/44809.

Notification of Transmittal of the International Search Report or the Declaration for PCT/US01/44809 dated May 8, 2003.

Written Opinion dated Dec. 24, 2003 for PCT/US02/38910.

Barry, P.W. et al. "In Vitro Comparison of the Amount of Salbutamol Available for Inhalation From Different Formulations Used with Different Spacer Devices" Eur Respir J 1997; 10: 1345–1348.

(List continued on next page.)

*Primary Examiner*—Glenn K. Dawson
*Assistant Examiner*—Michael Mendoza
(74) *Attorney, Agent, or Firm*—Burns, Doane, Swecker & Mathis, LLP

(57) ABSTRACT

A disposable aerosol generator for use with an inhaler device which includes a heater adapted to volatilize fluid stored in the disposable aerosol generator and method of using the inhaler. The disposable body includes a sealed chamber and an outlet, the chamber being located between first and second layers of material. The chamber holds a predetermined volume of a fluid which is expelled through the outlet when the fluid in the chamber is volatilized by the heater. The disposable body can include a series of spaced apart aerosol generators, each of which can be advanced to a release position at which the heater can heat one of the fluid containing chambers. Prior to heating the fluid, the outlet can be formed by severing the first and/or second layer with a piercing element and the volatilized fluid can be expelled from the outlet into a passage of a dispensing member.

21 Claims, 2 Drawing Sheets

U.S. PATENT DOCUMENTS 3,847,304 A 11/1974 Cohen
3,859,398 A 1/1975 Havstad
3,902,635 A 9/1975 Jinotti
3,903,883 A 9/1975 Pecina et al.
3,904,083 A 9/1975 Little
3,967,001 A 6/1976 Almaula et al.
3,987,941 A 10/1976 Blessing
3,993,246 A 11/1976 Erb et al.
4,012,471 A 3/1977 Kunkle, Jr.
4,012,472 A 3/1977 Lindsey
4,012,473 A 3/1977 Lindsey et al.
4,042,153 A 8/1977 Callahan et al.
4,060,082 A 11/1977 Lindberg et al.
4,077,542 A 3/1978 Petterson
4,161,282 A 7/1979 Erb et al.
4,162,501 A 7/1979 Mitchell et al.
4,215,708 A 8/1980 Bron
4,231,492 A 11/1980 Rios
4,258,073 A 3/1981 Payne
4,261,356 A 4/1981 Turner et al.
4,289,003 A 9/1981 Yang
4,291,838 A 9/1981 Williams
4,303,083 A 12/1981 Burruss, Jr.
4,383,171 A 5/1983 Sinha et al.
4,391,308 A 7/1983 Steiner
4,395,303 A 7/1983 Weir
4,433,797 A 2/1984 Galia
4,471,892 A 9/1984 Coleman
4,512,341 A 4/1985 Lester
4,575,609 A 3/1986 Fassel et al.
4,649,911 A 3/1987 Knight et al.
4,682,010 A 7/1987 Drapeau et al.
4,695,625 A 9/1987 Macdonald
4,700,657 A 10/1987 Butland
4,730,111 A 3/1988 Vestal et al.
4,735,217 A 4/1988 Gerth et al.
4,744,932 A 5/1988 Browne
4,749,778 A 6/1988 Fukuzawa et al.
4,753,352 A 6/1988 Dauphin et al.
4,762,995 A 8/1988 Browner et al.
4,776,515 A 10/1988 Michalchik
4,819,625 A 4/1989 Howe
4,819,834 A 4/1989 Thiel
4,829,996 A 5/1989 Noakes et al.
4,837,260 A 6/1989 Sato et al.
4,848,374 A 7/1989 Chard et al.
4,871,115 A 10/1989 Hessey
4,871,623 A 10/1989 Hoopman et al.
4,877,989 A 10/1989 Drews et al.
4,911,157 A 3/1990 Miller
4,922,901 A 5/1990 Brooks et al.
4,935,624 A 6/1990 Henion et al.
4,941,483 A 7/1990 Ridings et al.
4,947,875 A 8/1990 Brooks et al.
4,974,754 A 12/1990 Wirz
4,982,097 A 1/1991 Slivon et al.
4,992,206 A 2/1991 Waldron
5,021,802 A 6/1991 Allred
5,044,565 A 9/1991 Alexander
5,056,511 A 10/1991 Ronge
5,060,671 A 10/1991 Counts et al.
5,063,921 A 11/1991 Howe
5,096,092 A 3/1992 Devine
5,125,441 A 6/1992 Mette
5,133,343 A 7/1992 Johnson, IV et al.
5,134,993 A 8/1992 van der Linden et al.
5,135,009 A 8/1992 Müller et al.
5,144,962 A 9/1992 Counts et al.
5,151,827 A 9/1992 Ven et al.
5,178,305 A 1/1993 Keller
5,184,776 A 2/1993 Minier
5,217,004 A 6/1993 Blasnik et al.
5,226,441 A 7/1993 Dunmire et al.
5,228,444 A 7/1993 Burch
5,230,445 A 7/1993 Rusnak
5,231,983 A 8/1993 Matson et al.
5,259,370 A 11/1993 Howe
5,290,540 A 3/1994 Prince et al.
5,298,744 A 3/1994 Mimura et al.
5,299,565 A 4/1994 Brown
5,322,057 A 6/1994 Raabe et al.
5,327,915 A 7/1994 Porenski et al.
5,342,180 A 8/1994 Daoud
5,342,645 A 8/1994 Eisele et al.
5,349,946 A 9/1994 McComb
5,395,445 A 3/1995 Bohanan
5,421,489 A 6/1995 Holzner, Sr. et al.
5,462,597 A 10/1995 Jubran
5,474,059 A 12/1995 Cooper
5,515,842 A 5/1996 Ramseyer et al.
5,522,385 A 6/1996 Lloyd et al.
5,556,964 A 9/1996 Hofstraat et al.
5,564,442 A 10/1996 MacDonald et al.
5,565,677 A 10/1996 Wexler
5,575,929 A 11/1996 Yu et al.
5,585,045 A 12/1996 Heinonen et al.
5,617,844 A 4/1997 King
5,642,728 A 7/1997 Andersson et al.
5,674,860 A 10/1997 Carling et al.
5,682,874 A 11/1997 Grabenkort et al.
5,730,158 A 3/1998 Collins et al.
5,756,995 A 5/1998 Maswadeh et al.
5,765,724 A 6/1998 Amberg et al.
5,792,422 A 8/1998 Lin et al.
5,839,430 A 11/1998 Cama
5,855,202 A 1/1999 Andrade
5,856,671 A 1/1999 Henion et al.
5,863,652 A 1/1999 Matsumura et al.
5,869,133 A 2/1999 Anthony et al.
5,872,010 A 2/1999 Karger et al.
5,878,752 A 3/1999 Adams et al.
5,881,714 A 3/1999 Yokoi et al.
5,906,202 A 5/1999 Schuster et al.
5,914,122 A 6/1999 Otterbeck et al.
5,932,249 A 8/1999 Gruber et al.
5,932,315 A 8/1999 Lum et al.
5,934,272 A 8/1999 Lloyd et al.
5,934,273 A 8/1999 Andersson et al.
5,944,025 A 8/1999 Cook et al.
5,954,979 A 9/1999 Counts et al.
5,957,124 A 9/1999 Lloyd et al.
5,970,973 A 10/1999 Gonda et al.
5,970,974 A 10/1999 Van Der Linden et al.
5,978,548 A 11/1999 Holmstrand et al.
5,993,633 A 11/1999 Smith et al.
6,014,970 A 1/2000 Ivri et al.
6,053,176 A 4/2000 Adams et al.
6,054,032 A 4/2000 Haddad et al.
6,069,214 A 5/2000 McCormick et al.
6,069,219 A 5/2000 McCormick et al.
6,070,575 A 6/2000 Gonda et al.
6,071,428 A 6/2000 Franks et al.
6,076,522 A 6/2000 Dwivedi et al.
6,077,543 A 6/2000 Gordon et al.
6,080,721 A 6/2000 Patton
6,085,740 A 7/2000 Ivri et al.
6,085,753 A 7/2000 Gonda et al.
6,089,228 A 7/2000 Smith et al.
6,095,153 A 8/2000 Kessler et al.
6,098,615 A 8/2000 Lloyd et al.
6,098,620 A 8/2000 Lloyd et al.

| | | | |
|---|---|---|---|
| 6,103,270 | A | 8/2000 | Johnson et al. |
| 6,116,516 | A | 9/2000 | Gañán-Calvo |
| 6,116,893 | A | 9/2000 | Peach |
| 6,119,953 | A | 9/2000 | Gañán-Calvo et al. |
| 6,123,068 | A | 9/2000 | Lloyd et al. |
| 6,123,936 | A | 9/2000 | Platz et al. |
| 6,131,567 | A | 10/2000 | Gonda et al. |
| 6,131,570 | A | 10/2000 | Schuster et al. |
| 6,136,346 | A | 10/2000 | Eljamal et al. |
| 6,138,668 | A | 10/2000 | Patton et al. |
| 6,155,268 | A | 12/2000 | Takeuchi |
| 6,158,431 | A | 12/2000 | Poole |
| 6,158,676 | A | 12/2000 | Hughes |
| 6,159,188 | A | 12/2000 | Laibovitz et al. |
| 6,164,630 | A | 12/2000 | Birdsell et al. |
| 6,165,463 | A | 12/2000 | Platz et al. |
| 6,167,880 | B1 | 1/2001 | Gonda et al. |
| 6,174,469 | B1 | 1/2001 | Gañán-Calvo |
| 6,182,712 | B1 | 2/2001 | Stout et al. |
| 6,187,214 | B1 | 2/2001 | Gañán-Calvo |
| 6,187,344 | B1 | 2/2001 | Eljamal et al. |
| 6,189,803 | B1 | 2/2001 | Gañán-Calvo |
| 6,192,882 | B1 | 2/2001 | Gonda |
| 6,197,835 | B1 | 3/2001 | Gañán-Calvo |
| 6,205,999 | B1 | 3/2001 | Ivri et al. |
| 6,206,242 | B1 | 3/2001 | Amberg et al. |
| 6,207,135 | B1 | 3/2001 | Rössling et al. |
| 6,223,746 | B1 | 5/2001 | Jewett et al. |
| 6,230,706 | B1 | 5/2001 | Gonda et al. |
| 6,231,851 | B1 | 5/2001 | Platz et al. |
| 6,234,167 | B1 | 5/2001 | Cox et al. |
| 6,234,402 | B1 | 5/2001 | Gañán-Calvo |
| 6,235,177 | B1 | 5/2001 | Borland et al. |
| 6,250,298 | B1 | 6/2001 | Gonda et al. |
| 6,250,301 | B1 | 6/2001 | Pate |
| 6,257,233 | B1 | 7/2001 | Burr et al. |
| 6,258,341 | B1 | 7/2001 | Foster et al. |
| 6,263,872 | B1 | 7/2001 | Schuster et al. |
| 6,267,155 | B1 | 7/2001 | Parks et al. |
| 6,275,650 | B1 | 8/2001 | Lambert |
| 6,276,347 | B1 | 8/2001 | Hunt |
| 6,284,525 | B1 | 9/2001 | Mathies et al. |
| 6,288,360 | B1 | 9/2001 | Beste |
| 6,290,685 | B1 | 9/2001 | Insley et al. |
| 6,294,204 | B1 | 9/2001 | Rössling et al. |
| 6,295,986 | B1 | 10/2001 | Patel et al. |
| 6,318,361 | B1 | 11/2001 | Sosiak |
| 2001/0032647 | A1 | 10/2001 | Schuster et al. |

OTHER PUBLICATIONS

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994 (023).

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp 97–102.

Hou, Shuguang et al. *Solution Stability of Budensonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994) (023).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

DISPOSABLE AEROSOL GENERATOR SYSTEM AND METHODS FOR ADMINISTERING THE AEROSOL

BACKGROUND OF THE INVENTION

1. Field of the Invention

The present invention relates to an apparatus, system and methods of administering a fluid such as a medicated fluid in metered amount such as a unit dose to treat respiratory ailments. In particular, the invention relates to disposable aerosol generators, wherein the aerosols are generated via vaporization.

2. Description of Related Art

Aerosols are useful in a variety of applications including treatment of respiratory ailments. Various techniques for generating aerosols are disclosed in U.S. Pat. Nos. 4,811,731; 4,627,432; 5,743,251; and 5,823,178.

In particular, two distinct methods for delivery of medicated fluid in the form of an aerosol have been developed. In accordance with one method, a pharmaceutically active drug is dispensed in a low boiling point propellant (e.g., chloro-fluoro-carbon (CFC) or (HFA)) loaded in a pressurized canister from which the drug/propellant formulation may be released by the use of a device generally known as a metered dose inhaler. Once released the propellant evaporates and particles of the drug are inhaled by the patient. The other method involves the use of a nebulizer which creates an inhalable mist of fine particles from a solution or suspension of a drug. Both methods are hindered by significant problems relating to administering the proper dose.

In drug delivery applications, it is typically desirable to provide an aerosol having average mass median particles diameter of less than 2 microns to facilitate deep lung penetration. Additionally, it is desirable, in certain drug applications, to deliver medicaments at high flow rates (i.e., above 1 milligram per second). Devices for controlling the flow rate of an aerosol are known. For example, U.S. Pat. No. 4,790,305 concerns controlling the particle size of a metered dose of aerosol for delivery to the walls of bronchi and bronchioles by filling a first chamber with medication and a second chamber with air such that all of the air is inhaled prior to the inhaling of medication, and using flow control orifices to control the flow rate. U.S. Pat. No. 4,926,852 relates to metering a dose of medication into a flow-through chamber that has orifices to limit the flow rate to control particle size. U.S. Pat. No. 3,658,059 discloses a baffle that changes the size of an aperture in the passage of the suspension being inhaled to select the quantity and size of particles delivered. A problem associated with these devices is that they process the aerosol after it is generated and are inefficient and wasteful.

To meet the requirements of administering a fluid in the form of an aerosol and to overcome the disadvantages of the prior art, it is an object of the present invention to provide an aerosol generator which vaporizes the fluid at a controlled flow rate regardless of the fluid's viscosity.

It is another object of the invention to obtain uniform vaporization of the fluid that is expelled from the aerosol generator.

It is a further object of the invention to provide a disposable aerosol generator which can deliver a metered dose of the fluid. By delivering individual single doses of medicated fluid it is possible to avoid contamination of the fluid, thereby negating the need for bacteriostatic compounds within the drug formulation.

It is yet another object of the invention to provide a disposable cartridge which can incorporate a package having therein multiple disposable aerosol generators, each of which provides a single shot delivery, as required by the user.

Other objects and aspects of the present invention will become apparent to one of ordinary skill in the art upon review of the specification, drawings and claims appended hereto.

SUMMARY OF THE INVENTION

According to one aspect of the invention, a disposable aerosol generator is provided which is adapted for use with an inhaler device which includes a heater arranged to volatilize fluid stored in the disposable aerosol generator. The aerosol generator comprises a disposable body having a sealed chamber and an outlet wherein first and second layers of material define the chamber. The chamber accommodates a predetermined volume of a fluid which is expelled through the outlet when the fluid in the chamber is volatilized by the heater.

According to another aspect of the invention, an inhaler device is provided which is usable with the disposable aerosol generator mentioned above, the inhaler device including a heater arranged to heat the fluid in the chamber so as to expel volatilized fluid from the outlet. The heater can comprise a layer of resistance heating material on a substrate which includes an opening located adjacent the outlet. In order to form the outlet, an opening device such as a piercing element can be provided which is adapted to pierce the first and/or second layer to form the outlet.

According to a further aspect of the invention, a method of using the inhaler device mentioned above is provided, the method including severing the first and/or second layer so as to form the outlet and activating the heater so as to volatilize the fluid in the chamber and expel the volatilized fluid through the outlet. According to a preferred method, the disposable body includes a series of spaced apart aerosol generators and the method includes moving the disposable body relative to the inhaler device so as to locate a first one of the aerosol generators at a position where the heater can heat the fluid in the chamber of the first aerosol generator and volatilize the fluid therein. The severing can be carried out by driving a piercing member through the first and/or second layer and the outlet can be located adjacent a passage of a dispensing member such that the volatilized fluid formed by the heater is expelled into the passage after passing through the outlet.

BRIEF DESCRIPTION OF THE DRAWINGS

The objects and advantages of the invention will become apparent from the following detailed description of the preferred embodiments thereof in connection with the accompanying drawing, in which.

DETAILED DESCRIPTION OF THE PREFERRED EMBODIMENTS OF THE INVENTION

The present invention provides an inhaler effective for administering a fluid such as a medicated fluid in aerosol form. It has surprisingly and unexpectedly been determined that a metered amount of fluid can be delivered from the inhaler via a disposable aerosol generator wherein the fluid is fully vaporized and delivered at a predetermined flow rate.

Figure 1:
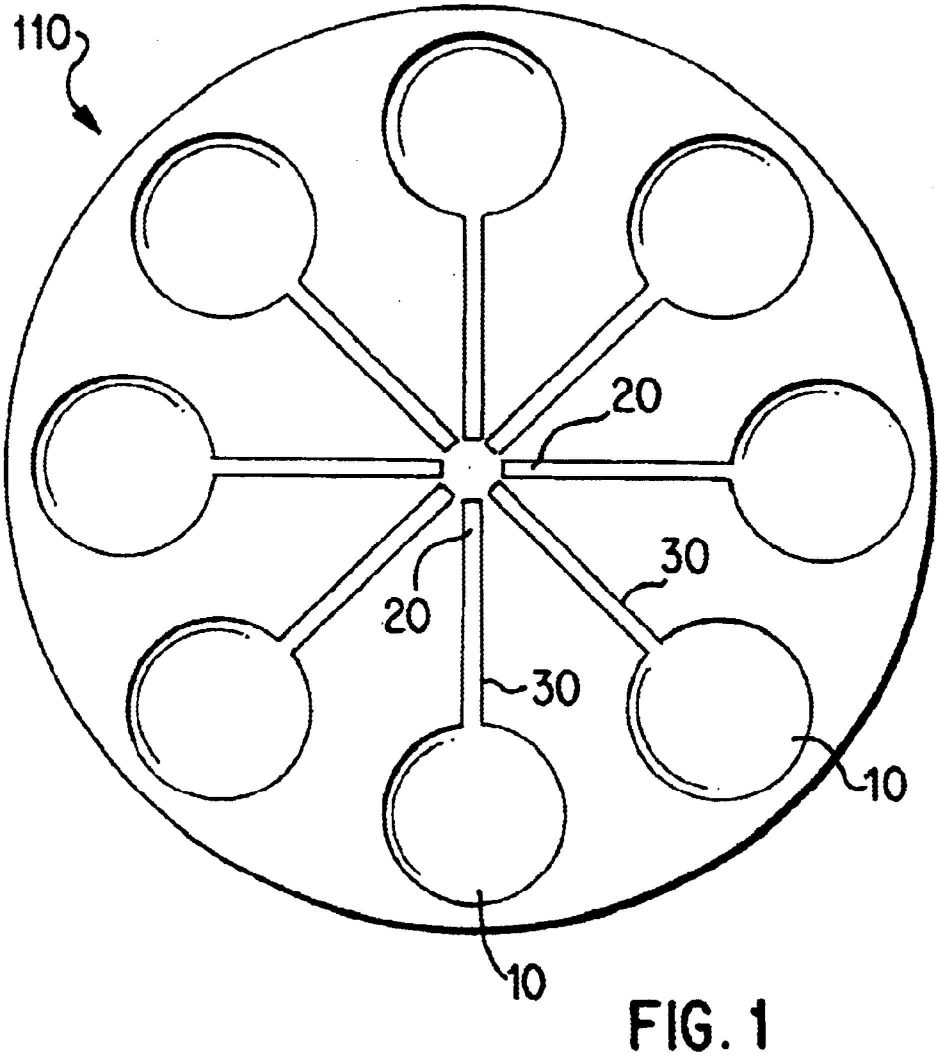
FIGS. 1 and 2 show details of a disposable body containing a series of aerosol generators according to one embodiment of the invention, FIG. 1 showing a top view thereof and FIG. 2 showing a side view thereof.
Figure 2:
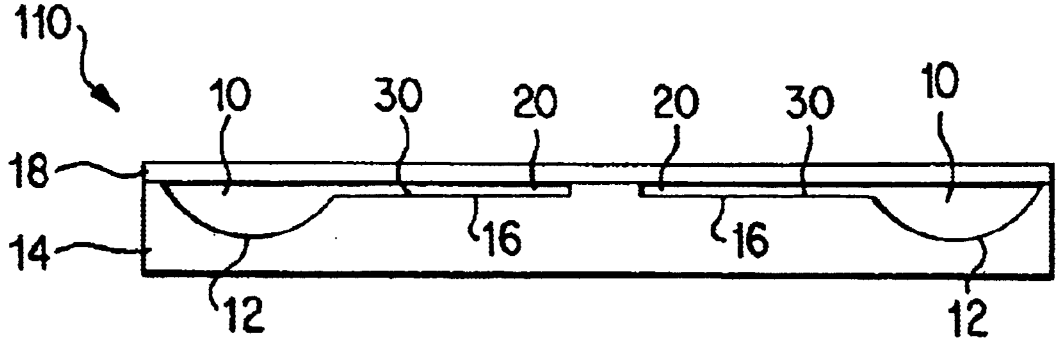
Figure 3:
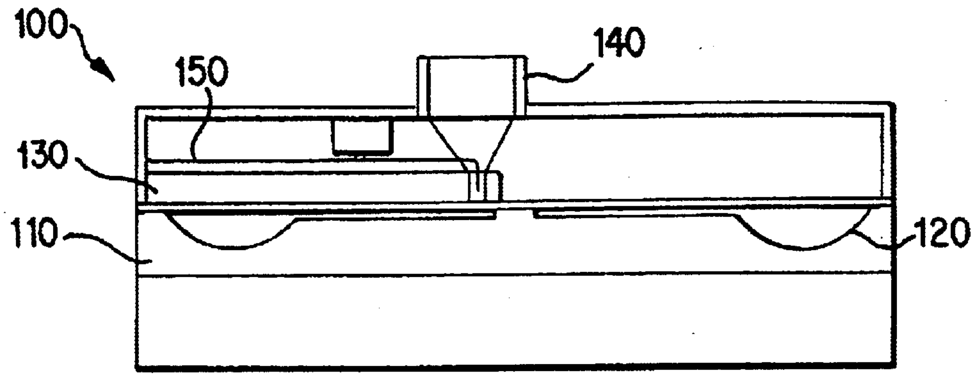
FIG. 3 shows an inhaler device according to an embodiment of the invention.
Figure 4:
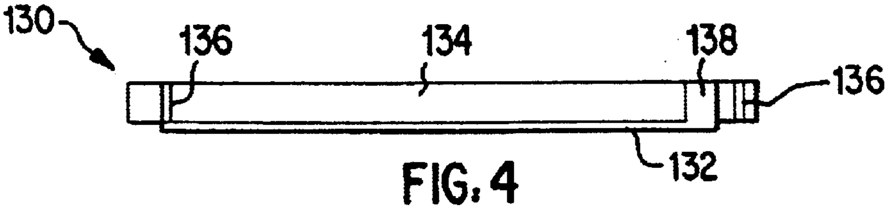
FIG. 4 shows details of a heater of the inhaler device shown in FIG. 3.

With reference to FIGS. 1 and 2, an aerosol generator in accordance with one embodiment of the present invention is shown schematically. A single shot chamber or reservoir 10 is designed to accommodate a predetermined volume of fluid which can incorporate a medicament for treating various respiratory ailments (e.g., a partial list includes albuterol, isoproterenol sulfate, metaproterenol sulfate, terbutaline sulfate, pirbuterol acetate, salmeterol xinotoate, formotorol; steroids including beclomethasone dipropionate, flunisolide, fluticasone, budesonide and triamcinolone acetonide, beclomethasone dipropionate, triameinolone acetonide, flunisolide and fluticasone, etc.). Of course, the volume and composition of fluid may be predicated on the amount desired to treat a particular medical ailment.

An outlet 20 is in fluid communication with the chamber 10 and a heating member (not shown) disposed on or in proximate location to either chamber 10 and/or outlet 20 is operable to vaporize the fluid in the chamber 10 and eject the vaporized fluid out of the outlet 20. For instance, a heating member may be employed in conjunction with both the chamber 10 and outlet 20. In a preferred embodiment, the heater comprises part of a reusable inhaler device. However, the heater can be incorporated in the disposable body, e.g., a resistance heating element heated by passing current therethrough or by inductively heating the heating element.

In accordance with a preferred embodiment of the invention, chamber 10 is constructed from a material (e.g., polymeric, aluminum foil) resistant to heating. For example, in the embodiment shown in FIGS. 1 and 2, the chamber 10 is formed as a recess 12 in an injection molded body 14 of polymer material and a flow passage 30 comprises a channel 16 in the body 14, the channel 16 extending from the recess 12. The chamber 10 is sealed by a layer 18 such as aluminum foil heat sealed to the body 14.

In order to provide multiple doses of medicated fluid in a disposable part of an inhaler, the body 14 can include a plurality of recesses 12. The laminate thus described is capable of withstanding the pressure applied to the interior of the chamber through the application of heat necessary to vaporize the fluid contained therein. Outlet 20 is preferably a small aperture at the end of the flow passage 30, the outlet being initially closed to the atmosphere. The flow passage 30 can have any suitable size which is effective to expel the vaporized fluid into the atmosphere and form the aerosol of desired particle size. For instance, flow passage 30 can have an inside diameter of about 0.05 to about 0.60 millimeter, preferably about 0.2 mm and a length of about 100 to 200 times the inside diameter. The chamber 10 can have any desired size such as a size suitable to deliver a single dose of medicated fluid, e.g., 5 $\mu$l.

In operation, the fluid in the chamber 10 is heated by a heating device which heats the fluid to a temperature sufficient to volatilize the fluid. In the case of an organic liquid material, the heating device preferably heats the fluid to approximately the boiling point, and preferably does not heat the fluid above 400° C., as most organic fluids are not stable when they are exposed to temperatures above 400° C.

Heating can be achieved in various ways including resistance or induction heating to heat the fluid via thermal conduction. Suitable heating devices envisioned for employment in the aerosol generator of the present invention include electrical resistance heaters, deposited resistance heating material such as thin platinum layers, electro-induction heating coils, etc. For example, the heating device can comprise an electrical resistance heater element arranged to thermally conduct heat into the chamber 10. The heater can be any suitable material such as platinum, tungsten, molybdenum or metal alloy such as an iron-based alloy having 71.7% (by weight) iron, 23% chromium, and 5.3% aluminum.

The flow passage 30 can have any desired configuration. For instance, the flow passage can have a uniform cross-sectional area along the length thereof between the chamber 10 and the outlet 20. However, the flow passage can vary in size along the length thereof, e.g., tapered so as to become more narrow in a direction towards the outlet 20. Further, the chamber need not comprise a concave circular recess, but rather can comprise any desired configuration sized to accommodate a single dose of the medicated fluid.

According to a preferred embodiment, the heater device can comprise a layer of resistance heating material deposited on the outside of a support member such as a plastic or ceramic member, e.g., alumina, glass, titania, zirconia, or yttria-stabilized zirconia which does not experience oxidation at normal operating temperatures.

The heater support and the heater layer preferably have a roughly matching coefficient of thermal expansion to minimize thermally induced delamination. Also, the ceramic support material can have a surface roughness to improve adhesion of the deposited heater layer. Platinum is desirable as a heater material in that it is resistant to oxidation degradation or other corrosion.

The heater layer can be deposited as a thin film on a ceramic support such that the heater layer has a thickness of, e.g., less than approximately 2 $\mu$m. The heater layer can be deposited onto the ceramic by any suitable method such as DC magnetron sputter deposition, e.g., using an HRC magnetron sputter deposition unit, in argon at $8.0 \times 10^{-3}$ Torr. Alternatively, other conventional techniques such as vacuum evaporation, chemical deposition, electroless plating, electroplating, and chemical vapor deposition can be employed to apply the heater layer to the substrate. It will be appreciated by those skilled in the art, that the energy produced by the heating device can be distributed optimally by tailoring the pattern of the thin film. For example, the heater pattern can be arranged to provide more heat near the outlet 20 than in the vicinity of the recess 12.

The closed end of the flow passage 20 can be opened by an opening device such as solenoid activated puncturing element. Alternatively, a cutting blade or scissors suitable for cutting the material sealing the flow passage 30 can be used to expel the volatilized fluid. It is further within the scope of the invention that other techniques such as a breakable seal can be employed on the closed end of the flow passage. The volatilized fluid can be expelled in a controlled manner taking into account properties of the fluid and the amount of heat needed to vaporize the fluid. The volatilized fluid can be expelled from the outlet 20 at a high velocity, e.g., approximately 90 m/s, but the volatilized fluid can be quickly dissipated in the atmosphere as the aerosol is formed from the condensing vapor, e.g., within about 2 mm of the outlet 20. The volatilized fluid can be mixed with ambient air in an inhaler mouthpiece surrounding the outlet 20, whereupon rapid cooling and condensation of the vapor result in formation of the aerosol.

The characteristics of the aerosol generated in accordance with the invention is a function of various parameters of the generator and the fluid provided. For aerosols intended for inhalation, for example, it is desirable for the aerosol to be approximately at body temperature when inhaled and for the mass media particles of the aerosol to be less than 2 microns, preferably between 0.5 and 1 micron.

Upon delivery of the metered amount of fluid, in aerosol form, the aerosol generator comprising the chamber 10, outlet 20 and flow passage 30 can be discarded. In the case where multiple generators are provided in a multidose cartridge such as the disposable body shown in FIGS. 1 and 2, the cartridge can be disposed of when the last of the individual chambers have been emptied.

In accordance with another preferred embodiment, the heating device can comprise a plurality of heating members arranged to heat the fluid in the chamber and/or along the flow passage. Also, the fluid in the chamber could be expelled mechanically, e.g., by a member which pushes the fluid into the flow passage and a heater along the flow passage can be used to volatilize the fluid and expel the vaporized fluid out of the outlet 20.

With reference to FIGS. 3–6, a fluid delivery system is depicted, wherein individual disposable aerosol generators are transported to a fluid release position as required by the user. The fluid delivery system 100 includes a cartridge 110 loaded with disposable aerosol generators 120. In a preferred embodiment, the aerosol generators 120 are provided in the form of packets, preferably constructed as described above in connection with FIGS. 1 and 2. A heating device 130 provides sufficient energy to each generator 120 to vaporize the fluid and expel the vaporized fluid through a passage in a dispenser 140. An opening device 150 can comprise a puncture element 152 activated by a solenoid 154, the puncture element 152 being operable by a suitable controller and circuitry to penetrate the layer 18 in the vicinity of outlet 20.

The heating device 130 includes an electrically resistive heating element 132 on a substrate 134, the heating element 132 being powered by electrically conductive connections 136 extending through vias in the substrate 134. The substrate 134 includes an opening 138 through which the piercing end of the puncture element 152 can move towards and away from the cartridge 110. In operation, the controller can be activated to operate the system 100 so as to rotate the cartridge 110 to a drug release position, actuate the solenoid to drive the puncture arm towards the cartridge so as to pierce the channel 16 and thereby form the outlet 20, and activate the heating element so as to heat the fluid in the chamber 10 whereby vaporized fluid is expelled through the dispenser 140.

Figure 5:
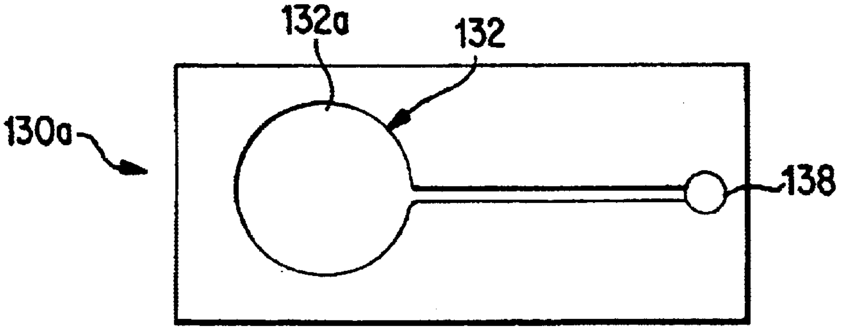
FIG. 5 shows details of a first heater element pattern which can be used for a resistance heating layer of the heater shown in FIG. 4.
Figure 6:
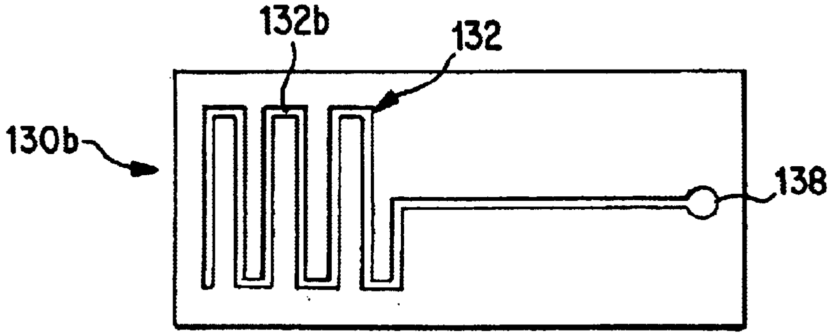
FIG. 6 shows details of a second heater element pattern which can be used for a resistance heating layer of the heater shown in FIG. 4.

FIGS. 5 and 6 show embodiments of different heater patterns for the heater 130. The heater 130*a* shown in FIG. 5 includes a heating element 132*a* configured to completely cover the chamber 10 and flow passage 30. With the heater element pattern shown in FIG. 5, greater heating can be achieved in the flow passage 30 due to the smaller cross sectional area of the heating element along the flow passage. The heater 132*b* shown in FIG. 6 includes a heating element 132*b* configured as a sinusoidally shaped strip which overlies chamber 10 and a rectilinear strip which overlies the flow passage 20.

In operation, the disposable cartridge 110 can be loaded into the inhaler 100, and a transport mechanism (not shown) can be operated to successively transport the aerosol generators to the release position at which the heater volatilizes the fluid contained in the respective chamber. Driving power for the transport mechanism, the solenoid and the heating element can be provided by a power source such as a 9-volt battery. The dispenser 140 can be arranged to supply the vaporized fluid to a mouthpiece (not shown) of the inhaler 100.

While the invention has been described in detail with reference to specific embodiments thereof, it will be apparent to those skilled in the art that various changes and modifications can be made, and equivalents employed, without departing from the scope of the appended claims.

What is claimed is:

1. A disposable aerosol generator for use with an inhaler device which includes a heater adapted to volatilize fluid stored in the disposable aerosol generator, comprising:

a disposable body including first and second layers of material and a series of spaced apart aerosol generators, each of the aerosol generators including a flow passage extending between a sealed chamber and an outlet which can be opened to expel volatilized fluid, the flow passage of each aerosol generator being located between the first and second layers, the disposable body being configured to fit in the inhaler device to allow advancement of each respective aerosol generator to a release position at which the fluid in the chamber of the respective aerosol generator can be heated, the chamber of each aerosol generator accommodating a predetermined volume of a fluid which is expelled as the volatilized fluid through the opened outlet when the fluid in the chamber is volatilized.

2. An inhaler device usable with the disposable aerosol generator according to claim 1, wherein the inhaler device includes a heater arranged to heat the fluid in the chamber of each respective aerosol generator or a respective one of the aerosol generators so as to expel volatilized fluid from the opened outlet.

3. The inhaler device according to claim 2, wherein the heater comprises an electrical resistance heater.

4. The inhaler device according to claim 3, wherein the heater comprises a layer of resistance heating material on a substrate, the substrate including an opening located adjacent the outlet of each respective aerosol generator or a respective one of the aerosol generators.

5. The inhaler device according to claim 2, further comprising an opening device, the opening device being adapted to pierce the first layer and/or second layer and open the outlet of each respective aerosol generator or a respective one of the aerosol generators.

6. The inhaler device according to claim 5, wherein the opening device includes a solenoid activated piercing element, the piercing element including a movable tip which is located in the opening in the substrate, the tip being moved upon actuation of the piercing element such that the tip penetrates the first layer of the disposable body.

7. The inhaler device according to claim 2, wherein the disposable body is movably supported such that the chamber of each respective aerosol generator or a respective one of the aerosol generators can be moved to a release position at which the heater can heat the fluid in the respective chamber sufficiently to volatilize the fluid to expel the volatilized fluid through the opened outlet.

8. The inhaler device according to claim 4, wherein the layer of resistance heating material comprises a strip arranged in a pattern which is coextensive with the size of the chamber.

9. The inhaler device according to claim 3, further comprising a dispensing member located adjacent the outlet of each respective aerosol generator or a respective one of the aerosol generators, the volatilized fluid expelled from the opened outlet passing through a passage in the dispensing member.

10. The inhaler device according to claim 2, wherein the first layer comprises a layer of polymer material and the second layer of material comprises a foil heat sealed to the polymer layer, the inhaler device including an opening member which is operable to pierce the foil layer to open the outlet of each respective aerosol generator or a respective one of the aerosol generators immediately prior to when the heater is activated to volatilize the fluid in the chamber of the respective aerosol generator.

11. The inhaler device according to claim 8, wherein the disposable body includes a flow passage extending rectilinearly from the chamber of each of the aerosol generators, the heater including a first portion arranged to heat the chamber and a second portion arranged to heat the flow passage of each respective aerosol generator or a respective one of the aerosol generators, the first and second portions of the heater comprising a layer of resistance heating material configured such that the second portion of the heater becomes hotter than the first portion of the heater during actuation of the heater to volatilize the fluid in the chamber of the respective aerosol generator.

12. A method of forming an aerosol using the inhaler device according to claim 3, comprising severing the first and/or second layer so as to open the outlet of each respective aerosol generator or a respective one of the aerosol generators and activating the heater so as to volatilize the fluid in the chamber and expel the volatilized fluid through the opened outlet of the respective aerosol generator.

13. The method according to claim 12, wherein the method comprises moving the disposable body relative to the inhaler device so as to locate a first one of the aerosol generators at a position where the heater can heat the fluid in the chamber of the first aerosol generator and volatilize the fluid therein.

14. The method according to claim 12, wherein the severing is carried out by driving a piercing member through the first and/or second layer, the outlet of each respective aerosol generator or a respective one of the aerosol generators being located adjacent a passage of a dispensing member and the volatilized fluid formed by the heater being expelled into the passage after passing through the opened outlet.

15. The method according to claim 14, wherein the disposable body includes a flow passage extending rectilinearly from the chamber of each of the aerosol generators, the heater including a first portion arranged to heat the chamber of each respective aerosol generator or a respective one of the aerosol generators and a second portion arranged to heat the flow passage of the respective aerosol generator, the first and second portions of the heater comprising a layer of resistance heating material configured such that the second portion of the heater becomes hotter than the first portion of the heater during volatilization of the fluid in the chamber.

16. The aerosol generator according to claim 4, wherein each of the chambers contains a predetermined volume of a fluid including at least one medicament selected from the group consisting of albuterol, isoproterenol sulfate, metaproterenol sulfate, terbutaline sulfate, pirbuterol acetate, salmeterol xinotoate, formotorol, beclomethasone dipropionate, flunisolide, fluticasone, budesonide, triamcinolone acetonide, beclomethasone dipropionate, triamcinolone acetonide, flunisolide and fluticasone.

17. The aerosol generator according to claim 12, wherein the fluid includes at least one medicament selected from the group consisting of albuterol, isoproterenol sulfate, metaproterenol sulfate, terbutaline sulfate, pirbuterol acetate, salmeterol xinotoate, formotorol, beclomethasone dipropionate, flunisolide, fluticasone, budesonide, triamcinolone acetonide, beclomethasone dipropionate, triamcinolone acetonide, flunisolide and fluticasone.

18. An inhaler device, comprising:

a disposable aerosol generator comprising a disposable body including a sealed chamber accommodating a fluid and a flow passage in communication with the chamber, the disposable body including first and second layers of material defining the chamber, the flow passage having an outlet which can be opened to expel volatilized fluid and having a diameter of from about 0.05 mm to about 0.60 mm; and a heater arranged to heat the fluid while in the chamber so as to expel volatilized fluid from the opened outlet.

19. An inhaler device, comprising:

a disposable aerosol generator comprising a disposable body including a sealed chamber accommodating a fluid and a flow passage in communication with the chamber, the disposable body including first and second layers of material defining the chamber, the flow passage having an outlet which can be opened to expel volatilized fluid and having a width of from about 0.05 mm to about 0.60 mm; and a heater arranged to heat the fluid while in the chamber so as to expel volatilized fluid from the opened outlet.

20. The inhaler device according to claim 18, wherein the chamber contains a predetermined volume of a fluid including at least one medicament selected from the group consisting of albuterol, isoproterenol sulfate, metaproterenol sulfate, terbutaline sulfate, pirbuterol acetate, salmeterol xinotoate, formotorol, beclomethasone dipropionate, flunisolide, fluticasone, budesonide, triamcinolone acetonide, beclomethasone dipropionate, triamcinolone acetonide, flunisolide and fluticasone.

21. The inhaler device according to claim 19, wherein the chamber contains a predetermined volume of a fluid including at least one medicament selected from the group consisting of albuterol, isoproterenol sulfate, metaproterenol sulfate, terbutaline sulfate, pirbuterol acetate, salmeterol xinotoate, formotorol, beclomethasone dipropionate, flunisolide, fluticasone, budesonide, triamcinolone acetonide, beclomethasone dipropionate, triamcinolone acetonide, flunisolide and fluticasone.

* * * * *

UNITED STATES PATENT AND TRADEMARK OFFICE

CERTIFICATE OF CORRECTION

PATENT NO. : 6,799,572 B2
DATED : October 5, 2004
INVENTOR(S) : Walter Allen Nichols et al.

It is certified that error appears in the above-identified patent and that said Letters Patent is hereby corrected as shown below:

<u>Column 3,</u>
Line 24, "triameinolone" should read -- triamcinolone --; and

<u>Column 7,</u>
Line 5, "claim 3" should read -- claim 2 --.

Signed and Sealed this

Second Day of August, 2005

JON W. DUDAS
*Director of the United States Patent and Trademark Office*